United States Patent
Hietbrink et al.

(10) Patent No.: US 10,618,614 B2
(45) Date of Patent: *Apr. 14, 2020

(54) VESSEL HAVING A COMPARTMENT FOR CONTAINING WATER

(71) Applicant: KONINKLIJKE PHILIPS N.V., Eindhoven (NL)

(72) Inventors: Roelant Boudewijn Hietbrink, Utrecht (NL); Bart Andre Salters, Eindhoven (NL); Esther Anna Wilhelmina Gerarda Janssen, Waalre (NL); Cornelis Gerardus Visser, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 0 days.

This patent is subject to a terminal disclaimer.

(21) Appl. No.: 16/427,774

(22) Filed: May 31, 2019

(65) Prior Publication Data
US 2019/0283847 A1    Sep. 19, 2019

Related U.S. Application Data (62) Division of application No. 15/771,011, filed as application No. PCT/EP2016/075001 on Oct. 19, 2016, now Pat. No. 10,407,141.

(30) Foreign Application Priority Data

Oct. 28, 2015  (EP) .................................... 15191866

(51) Int. Cl.
*B63B 59/04* (2006.01)
*B63B 13/00* (2006.01)
(Continued)

(52) U.S. Cl.
CPC ................ *B63B 59/04* (2013.01); *A61L 2/10* (2013.01); *B63B 3/66* (2013.01); *B63B 13/00* (2013.01);
(Continued)

(58) Field of Classification Search
CPC ......... B63B 13/00; B63B 59/04; B63B 59/08; B63B 3/66; A61L 2/10; A61L 2/0011
See application file for complete search history.

(56) References Cited

U.S. PATENT DOCUMENTS

| 5,308,505 A | 5/1994 | Titus et al. |
| 5,322,569 A | 6/1994 | Titus et al. |

(Continued)

FOREIGN PATENT DOCUMENTS

| DE | 102007057214 A1 | 6/2009 |
| WO | 2014014779 A1 | 1/2014 |

OTHER PUBLICATIONS

Bueley, C., "Ultraviolet Light as a Marine Antifoulant", AML Oceanographic, 2014.

*Primary Examiner* — Stephen P Avila (57) ABSTRACT

A vessel has a compartment (34) for containing water, which compartment (34) has at least one opening (31) in a wall (30) thereof for allowing water to pass therethrough. The compartment (34) comprises an assembly (1) of a grating (10) and at least one anti-biofouling source (20), the grating (10) being positioned in the opening (31) for blocking items from passing through the opening (31) along with the water, and comprising a number of elements and spaces between the elements, and the anti-biofouling source (20) being configured to emit ultraviolet light during operation thereof for realizing anti-biofouling of at least a portion of the grating (10). At least one of the elements of the grating (10) is at least partially transparent to the ultraviolet light, enabling a (Continued)

design of the assembly (1) in which anti-biofouling of the entire grating (10) may be guaranteed.

13 Claims, 3 Drawing Sheets

(51) Int. Cl.
  *B63J 4/00* (2006.01)
  *A61L 2/10* (2006.01)
  *B63B 3/66* (2006.01)
  *A61L 2/00* (2006.01)
  *B63B 13/02* (2006.01)
  *B63B 59/08* (2006.01)
(52) U.S. Cl.
  CPC ............... *B63J 4/00* (2013.01); *B63J 4/002* (2013.01); *A61L 2/0011* (2013.01); *B63B 13/02* (2013.01); *B63B 59/08* (2013.01); *B63B 2013/005* (2013.01)

(56) References Cited

U.S. PATENT DOCUMENTS

| | | |
|---|---|---|
| 5,478,527 A | 12/1995 | Gustafson |
| 8,502,165 B2 | 8/2013 | Lee |
| 2009/0136180 A1 | 5/2009 | Lee |
| 2010/0300982 A1 | 12/2010 | Nilsen |
| 2014/0078584 A1 | 3/2014 | Farr et al. |
| 2014/0196745 A1 | 7/2014 | Whelan |
| 2016/0340210 A1 | 11/2016 | Nilsen |

VESSEL HAVING A COMPARTMENT FOR CONTAINING WATER

CROSS-REFERENCE TO PRIOR APPLICATIONS

This Application is a Divisional Application of U.S. Ser. No. 15/771,011, filed Apr. 25, 2018, which is the U.S. National Phase application under 35 U.S.C. § 371 of International Application No. PCT/EP2016/075001, filed on Oct. 19, 2016, which claims the benefit of European Patent Application No. 15191866.1, filed on Oct. 28, 2015. These applications are hereby incorporated by reference herein.

FIELD OF THE INVENTION

The invention relates to a vessel having a compartment for containing water, which compartment is delimited by a portion of the vessel's hull and an interior wall arrangement of the vessel connecting to the hull, and which compartment has at least one opening in a wall thereof for allowing water to pass therethrough, wherein the compartment comprises a grating which is positioned in the opening for blocking items from passing through the opening along with the water, and which comprises a number of elements and spaces between the elements.

BACKGROUND OF THE INVENTION

In many practical cases, a ship, which is a practical embodiment of a vessel, has one or more compartments for containing water, which are partially delimited by the ship's hull, wherein the hull is provided with one or more openings at the position of each of the compartments for allowing exchange of water between the compartments and the ship's environment. Such compartments, which are often referred to as sea chests, may be used for taking in water to be used as ballast water or fire extinguishing water, for example. According to another possibility, assuming that the ship is of the engine-driven type, one or more sea chests may be used for accommodating a so-called box cooler for cooling the fluid of an engine cooling system of the ship, in which case the ship's hull is provided with openings for enabling a continuous flow of water through the sea chests and thereby achieving an effective cooling effect as desired. Usually, a box cooler as may be present in a sea chest comprises a plurality of tubes for containing and transporting the fluid to be cooled in their interior, wherein entry and exit openings are arranged in the hull at the position of the sea chest so that water can enter the sea chest, flow over the tubes in the sea chest, and exit the sea chest through natural flow and/or under the influence of motion of the ship.

In order to allow a sufficient flow of water through an opening of a sea chest on the one hand and to prevent items (including marine animals) which are small enough to pass through the opening from entering the sea chest on the other hand, it is practical for the opening to be equipped with a grating. As is generally known, a grating comprises one or more elements which are suitable for serving as a barrier extending in an opening. Normally, such elements have an elongated shape. In case a grating comprises a plurality of elements, the elements are often positioned in a regularly spaced arrangement. Basically, a grating comprising a plurality of elements may comprise a single set of the elements, wherein the elements are arranged in parallel, extending in a certain direction. However, it is also possible for a grating comprising a plurality of elements to comprise two sets of parallel elements, wherein the elements of the two sets extend in perpendicular directions. In any case, the size of the spaces between adjacent elements of a grating determines the size of items to be blocked by the grating.

Especially in case a grating is used in a marine environment, it may happen that the grating gets clogged as time passes, which hinders the flow of water through the opening in which the grating is present, and which may eventually result in total blockage of the opening. Such clogging is caused by a well-known phenomenon called biological fouling or biofouling.

In general, biofouling is the accumulation of microorganisms, plants, algae, small animals and the like on surfaces. According to some estimates, over 1,800 species comprising over 4,000 organisms are responsible for biofouling. Hence, biofouling is caused by a wide variety of organisms, and involves much more than an attachment of barnacles and seaweeds to surfaces. Biofouling is divided into micro biofouling which includes biofilm formation and bacterial adhesion, and macro biofouling which includes the attachment of larger organisms. Due to the distinct chemistry and biology that determine what prevents them from settling, organisms are also classified as being hard or soft. Hard biofouling organisms include calcareous organisms such as barnacles, encrusting bryozoans, mollusks, polychaetes and other tube worms, and zebra mussels. Soft biofouling organisms include non-calcareous organisms such as seaweed, hydroids, algae and biofilm "slime". Together, these organisms form a biofouling community.

In several situations, biofouling creates substantial problems. Biofouling can cause machinery to stop working, water inlets to get clogged, and heat exchangers to suffer from reduced performance. Hence, the topic of anti-biofouling, i.e. the process of removing or preventing biofouling, is well-known. In industrial processes involving wetted surfaces, bio dispersants can be used to control biofouling. In less controlled environments, biofouling organisms are killed or repelled with coatings using biocides, thermal treatments or pulses of energy. Nontoxic mechanical strategies that prevent organisms from attaching to a surface include choosing a material or coating for causing the surface to be slippery, or creating nanoscale surface topologies similar to the skin of sharks and dolphins which only offer poor anchor points. As an alternative, ultraviolet light may be used for removing/preventing the formation of biofilm on wet surfaces. For example, WO 2014/014779 discloses a system for reducing biofouling of a surface of an optically transparent element subjected to a marine environment, including an LED for emitting ultraviolet radiation, a mount for directing emitted ultraviolet radiation toward the optically transparent element, and control circuitry for driving the LED.

U.S. Pat. No. 5,308,505 discloses an anti-biofouling system for use with a grating. During operation of the anti-biofouling system, the grating is illuminated with ultraviolet light for the purpose of keeping the grating holes and the grating surface free from biofouling.

SUMMARY OF THE INVENTION

It is an object of the invention to provide anti-biofouling measures which are applicable to a grating used in an opening of a vessel's compartment, which are effective yet considerably less harmful to the environment than some of the known measures, and which have relatively uncomplicated constructions or are not so much susceptible to damage. According to the invention, a vessel having a compartment as defined in the opening paragraph, which compartment comprises a grating as mentioned, comprises an assembly of the grating and at least one anti-biofouling source, wherein the anti-biofouling source is configured to emit ultraviolet light during operation thereof for realizing anti-biofouling of at least a portion of the grating, and wherein at least one of the elements of the grating is at least partially transparent to the ultraviolet light.

In the context of the invention, anti-biofouling of at least a portion of the grating is realized on the basis of applying at least one anti-biofouling source which is configured to emit ultraviolet light during operation thereof, and which may comprise at least one light source such as an LED, for example. The grating is adapted to allow the ultraviolet light to pass through at least a portion of the elements thereof, wherein at least one of the elements of the grating is at least partially transparent to the ultraviolet light, on the basis of which several advantageous options are obtained in respect of the positioning of the at least one anti-biofouling source with respect to the grating, as will be explained in the following. In any case, by having a grating which at least partially does not block a transfer of the ultraviolet light, the anti-biofouling effects obtained by operating the anti-biofouling source are enhanced with respect to a situation in which a conventional grating is used. In particular, by having an appropriate design of the grating, wherein at least portions of the grating at strategic positions are transparent for allowing the ultraviolet light to pass through the grating at those portions, it is possible to reach more portions of the grating than as would be the case with a non-transparent grating, without needing to apply more anti-biofouling sources. In other words, according to the invention, the at least one anti-biofouling source can be applied for keeping the grating clean in a more efficient manner, not by modifying the anti-biofouling source in some way and/or increasing the number of anti-biofouling sources, but by adapting the design of the grating.

A well-known example of a vessel is a ship, and a well-known example of a compartment which is positioned directly adjacent the ship's hull is a so-called sea chest as mentioned in the foregoing. It is noted that in the context of the invention, the term "compartment" should preferably be understood such as to at least cover any area, space, chamber or basin which is at least partially delimited by a wall in which an opening is arranged for allowing water to pass therethrough, from the compartment to outside of the compartment, and/or in the opposite direction, whatever the case may be.

For the sake of clarity, it is noted that the word "grating" as used in this text should be understood such as to be applicable to the material appearance of the grating, i.e. the actual construction of the grating with the elements of the grating, rather than being applicable to the concept of a grating in a more general sense, which also includes the spaces as present between the elements of the grating. Thus, when the grating is said to be at least partially transparent to the ultraviolet light, or when a similar formulation is used, this should be understood such as to mean that the entire construction of actual elements constituting the grating is at least partially transparent, which implies that at least part of the material as present in the grating is transparent. Also, this means that at the level of the elements, it may be so that some or all of the construction elements are at least partially transparent, in conformity with what is mentioned earlier.

In a practical embodiment, the grating comprises a carrier frame and portions which are transparent to the ultraviolet light, the transparent portions being distributed over the carrier frame. The carrier frame can comprise material which is not transparent to the ultraviolet light, and can be made of metal, for example, or any other type of material which is commonly used in the field of gratings. By having a combination of materials in the grating, it is possible to realize a partially transparent character of the grating without necessarily decreasing constructional strength of the grating, while a possible increase of costs of the grating can be kept to a minimum. Advantageously, the transparent portions are distributed over the carrier frame, so as to have both the effect of ultraviolet light being allowed to pass through and the necessary constructional strength throughout the grating. Materials which are suitable for use in the transparent portions include quartz, silicones and calcium fluoride. It may particularly be advantageous for the transparent portions to be transparent to ultraviolet light having a wavelength in a range of 250 nm to 300 nm.

On the basis of the transparent character of at least a portion of the grating, it is possible for the anti-biofouling source to be integrated in the grating and still be capable of performing its anti-biofouling function on at least a portion of the grating. The fact is that the ultraviolet light is allowed to pass through the grating at the areas where the grating is transparent. In a conventional situation, the ultraviolet light would not be allowed to travel far through the grating, as the ultraviolet light would be blocked by elements of the grating. Hence, in such a situation, especially when the grating comprises two sets of parallel elements, wherein the elements of the two sets extend in perpendicular directions, integrating the anti-biofouling source in the grating would not help much in realizing anti-biofouling of the grating, unless an anti-biofouling source would be arranged in every mesh opening of the grating, which is expensive and not practical. Contrariwise, the invention offers a cost-effective and practical solution, wherein the number of anti-biofouling sources to be applied with the grating can be kept to a minimum, and wherein it is not necessary to have one or more anti-biofouling sources at a position outside of the grating, which is advantageous when it comes to protecting the anti-biofouling sources from getting damaged.

The number of anti-biofouling sources to be used with the grating can be chosen freely according to desire. The number of anti-biofouling sources can range from one anti-biofouling source to a plurality of anti-biofouling sources, all of which can be integrated in the grating.

According to an option which may be applied as an alternative of the option of integrating one or more anti-biofouling sources in the grating, or as an addition to that option, at least one anti-biofouling source of the assembly can be positioned inside the compartment. In such case, it is possible for the at least one anti-biofouling source which is positioned inside the compartment to be associated with a wall of the compartment, for example.

In case the grating comprises a carrier frame and transparent portions distributed over the carrier frame, it is very practical for the anti-biofouling source to be integrated in the carrier frame. Also in such case, the number of anti-biofouling sources to be used with the grating may range from one anti-biofouling source to a plurality of anti-biofouling sources.

For the sake of completeness, the following is noted in respect of anti-biofouling by using ultraviolet light. The anti-biofouling source for producing the ultraviolet light may comprise a light source which is chosen to specifically emit ultraviolet light of the c type, which is also known as UVC light, and even more specifically, light with a wavelength roughly between 250 nm and 300 nm. It has been found that most biofouling organisms are killed, rendered inactive, or rendered unable to reproduce by exposing them to a certain dose of the ultraviolet light. A typical intensity which appears to be suitable for realizing anti-biofouling is 10 mW per square meter, to be applied continuously or at a suitable frequency. A very efficient source for producing UVC light is a low pressure mercury discharge lamp, in which an average of 35% of input power is converted to UVC power. Another useful type of lamp is a medium pressure mercury discharge lamp. The lamp may be equipped with an envelope of special glass for filtering out ozone-forming radiation. Furthermore, a dimmer may be used with the lamp if so desired. Other types of useful UVC lamps are dielectric barrier discharge lamps, which are known for providing very powerful ultraviolet light at various wavelengths and at high electrical-to-optical power efficiencies, and LEDs. In respect of the LEDs, it is noted that they can generally be included in relatively small packages and consume less power than other types of light sources. LEDs can be manufactured to emit (ultraviolet) light of various desired wavelengths, and their operating parameters, most notably the output power, can be controlled to a high degree.

The light sources for emitting ultraviolet light can be provided in the form of a tubular lamp, more or less comparable to a well-known TL (tube luminescent/fluorescent) lamp. For various known germicidal tubular UVC lamps, the electrical and mechanical properties are comparable to those properties of tubular lamps for producing visible light. This allows the UVC lamps to be operated in the same way as the well-known lamps, wherein an electronic or magnetic ballast/starter circuit may be used, for example.

A general advantage of using ultraviolet light for realizing anti-biofouling is that the microorganisms are prevented from adhering and rooting on a surface to be kept clean. Contrariwise, when known poison dispersing coatings are applied, the anti-biofouling effect is achieved by killing the microorganisms after they have adhered and rooted on the surface. Prevention of biofouling by means of light treatment is preferred over removal of biofouling by means of light treatment, as the latter requires more input power and involves a higher risk that the light treatment is not sufficiently effective. In view of the fact that the light sources for producing ultraviolet light may be arranged and configured such that only a relatively low level of input power is needed, the light sources may be operated to continuously produce anti-biofouling light across a large surface without extreme power requirements, or the light sources may be operated at a duty cycle, wherein the light sources are on for a certain percentage of a time interval, and off for the rest of the time interval, wherein the time interval may be chosen to be in the order of magnitude of minutes, hours, or whatever is appropriate in a given situation. As not much additional power is required, the light sources can be easily applied in existing structures.

When the invention is applied, at least one ultraviolet light source is used for realizing anti-biofouling of a grating which is at least partially transparent to the ultraviolet light emitted by the light source during operation thereof. The light source may be arranged at any suitable position with respect to the grating, which position may be outside of the grating or integrated in the grating. In case at least two light sources are used, all light sources may be positioned outside of the grating, all light sources may be integrated in the grating, or one portion of the light sources may be positioned outside of the grating whereas the other portion of the light sources may be integrated in the grating. An advantage of integrating a light source in the grating is that in comparison with having a light source outside of the grating, the risk of the light source getting damaged is relatively low.

The above-described and other aspects of the invention will be apparent from and elucidated with reference to the following detailed description of two embodiments of an assembly for use with an opening of a ship's hull, comprising a grating and at least one anti-biofouling source for emitting ultraviolet light during operation thereof for realizing anti-biofouling of at least a portion of the grating. The embodiments are just two examples of numerous possible embodiments existing within the framework of the invention.

BRIEF DESCRIPTION OF THE DRAWINGS

The invention will now be explained in greater detail with reference to the figures, in which equal or similar parts are indicated by the same reference signs, and in which.

The figures are of a diagrammatical nature only and are not drawn to scale. For example, in FIG. 2, for the sake of illustrating the assembly according to the invention, the assembly is depicted on a relatively large scale whereas the compartment is depicted on a relatively small scale.

DETAILED DESCRIPTION OF EMBODIMENTS

Figure 1:
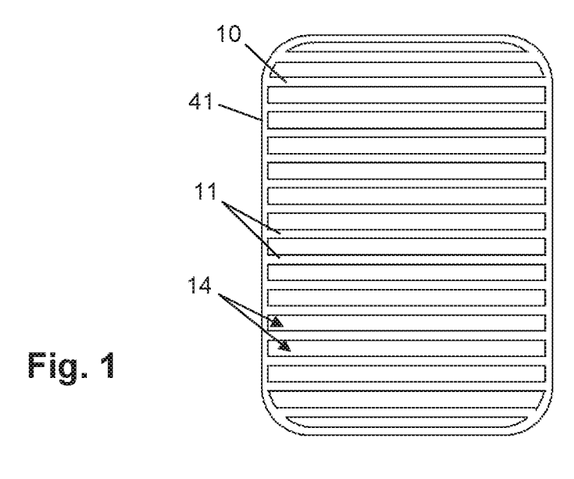
FIGS. 1 to 3 relate to an assembly of a grating and at least one anti-biofouling source according to a first embodiment of the invention in which the at least one anti-biofouling source is arranged outside of the grating, the figures showing the assembly as used with an opening of a ship's hull, wherein FIG. 1 diagrammatically shows a front view of the grating, FIG. 2 diagrammatically shows a side view of the assembly and a compartment of the ship as partially delimited by the ship's hull, and FIG. 3 diagrammatically shows a side view of a portion of the grating.
Figure 2:
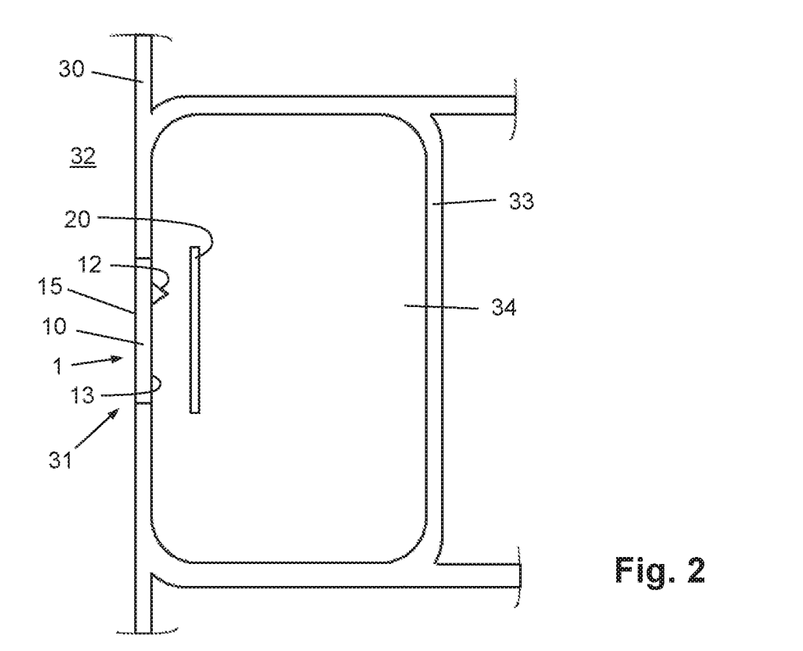
Figure 3:
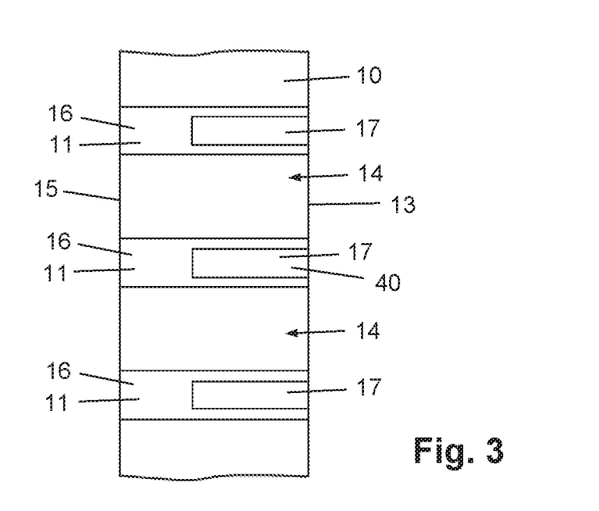

FIGS. 1 to 3 relate to an assembly 1 of a grating 10 and at least one anti-biofouling source 20 according to a first embodiment of the invention in which the at least one anti-biofouling source 20 is arranged outside of the grating 10, the figures showing the assembly 1 as used with an opening 31 of a ship's hull 30, wherein the grating 10 is arranged in the opening 31 so as to block items from passing through the opening 31.

In general, an opening 31 in a ship's hull 30 has a function in allowing exchange of water between the immediate environment 32 of the ship and a compartment of the ship as delimited by a portion of the ship's hull 30 and an interior wall arrangement 33 of the ship connecting to the hull 30, which is shown in FIG. 2, and which will hereinafter be denoted as sea chest 34. For example, the sea chest 34 may be used as a compartment for taking in water to be used as fire extinguishing water, or as a compartment for accommodating a box cooler which is enabled to perform its cooling function by continuous exposure to fresh water from the ship's environment 32 during operation. In order to prevent items such as fishes and other marine animals, algae, waste floating in the water etc. from entering the sea chest 34 along with an incoming flow of water, it is commonly known to provide a grating 10 and fit the grating 10 in every opening 31 providing access to the sea chest 34.

Usually, a grating 10 comprises at least one element which is arranged such as to be capable of serving as a barrier in the opening 31 in which the grating 10 is fitted. In fact, a grating 10 is adapted to divide an opening 31 in at least two openings of smaller size. In the shown example, the grating 10 comprises a plurality of elements 11 having an elongated shape and extending substantially parallel with respect to each other, in a regularly spaced arrangement. However, that does not alter the fact that the invention is equally applicable to any other possible type of grating, including the type comprising two sets of substantially parallel elements, wherein the elements of the two sets extend in perpendicular directions. Also, it is noted that in many practical cases, including the case as illustrated in FIG. 1, the grating 10 comprises elements which are arranged such as to form a peripheral rim 41 of the grating 10. Advantageously, as shown in FIG. 2, the grating 10 comprises a hinge 12, so that the grating 10 may be put to a tilted position for purposes of cleaning and/or maintenance, for example. The use of a hinge 12 with a grating 10 for openings 31 in a ship's hull 30 is well known, and will not be further explained here. For obvious reasons, the hinge 12 is present at the side of the grating 10 facing the sea chest 34, which will hereinafter be referred to as interior side 13.

Spaces 14 between two adjacent elements 11 of the grating 10 are relatively small, so that the grating 10 is effective in allowing only water to enter the sea chest 34 from the outside, while preventing objects as may be present in the water to enter the sea chest 34 as well. However, on the basis of this fact, there is a considerable risk of clogging of the grating 10, especially under the influence of biofouling. In order to significantly reduce this risk, at least one anti-biofouling source 20 is provided, which serves for emitting ultraviolet light during operation thereof, whereby it is possible to realize anti-biofouling of at least a portion of the grating 10. The ultraviolet light may be of the type known as UVC light, which is known to be effective for realizing anti-biofouling of surfaces. The anti-biofouling source 20 may be operated continuously, but it also possible to operate the anti-biofouling source 20 at certain intervals only, wherein the ultraviolet light may be dosed at a suitable intensity. The assembly 1 according to the first embodiment of the invention comprises at least one anti-biofouling source 20 which is arranged outside of the grating 10, at a position for covering at least a considerable portion of the grating 10 by the ultraviolet light to be emitted during operation. In the shown example, the anti-biofouling source 20 has an elongated tubular shape and is arranged inside the sea chest 34 at a certain distance with respect to the grating 10, extending substantially parallel to the grating 10, in a direction which is substantially perpendicular to a direction in which the elements 11 of the grating 10 extend. Any suitable type of construction may be used for fixing the anti-biofouling source 20 at the appropriate position inside the sea chest 34.

In view of the fact that the anti-biofouling source 20 is arranged inside the sea chest 34, the interior side 13 of the grating 10 facing the sea chest 34 is under the direct influence of the anti-biofouling source 20. Hence, the anti-biofouling effect on this side of the grating 10 would be much stronger than on the other side of the grating 10, which will hereinafter be referred to as exterior side 15, if it would not be for measures according to the invention, which involve designing the grating 10 in such a way as to be at least partially transparent to the ultraviolet light. In this way, a situation in which the grating 10 clogs at the exterior side 15 thereof is prevented without a need for arranging another anti-biofouling source 20 at that side of the grating 10, which would cause additional friction of movement of the ship and which would be very vulnerable to mechanical impact.

In the first embodiment of the assembly 1 according to the invention, the elements 11 of the grating 10 are partially transparent and partially non-transparent. FIG. 3 illustrates the fact that the elements 11 comprise a combination of a transparent portion 16 and a non-transparent portion 17. The non-transparent portions 17 of the elements 11 may be made of a relatively strong material such as steel in order to serve as enforcement of the grating 10. Thus, the grating 10 may comprise a carrier frame 40 which is composed of the non-transparent portions 17 of the elements 11 and the elements forming the peripheral rim 41 of the grating 10. In the shown example, the arrangement of transparent portions 16 and non-transparent portions 17 is chosen such as to have an optimum of constructional strength and permeability to ultraviolet light. In particular, the non-transparent portions 17 are present at the interior side 13 of the grating 10, and extend in the direction of the exterior side 15 along only a portion of the distance between the two sides 13, 15 of the grating 10, while being embedded in the transparent portions 16.

Figure 4:
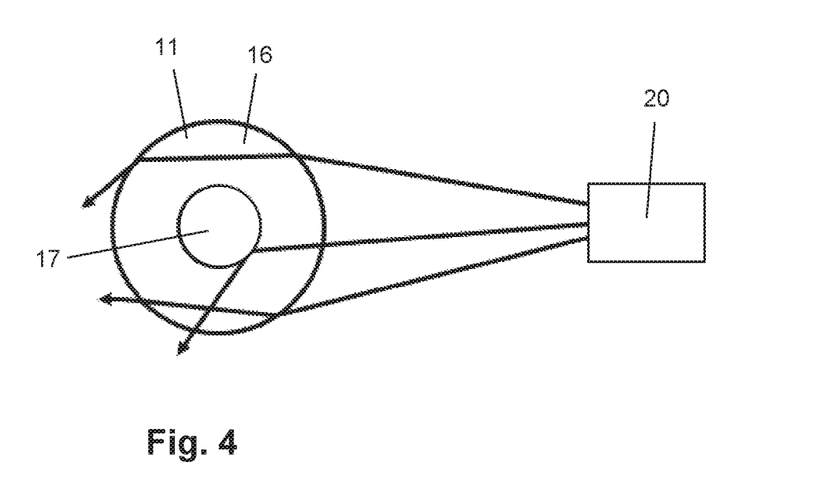
FIG. 4 illustrates examples of the way in which rays of ultraviolet light emitted by the anti-biofouling source during operation thereof may travel through an element of the grating.

In the assembly 1 according to the first embodiment of the invention, anti-biofouling of the grating 10 is realized by operating the anti-biofouling source 20 arranged inside the sea chest 34 so as to emit ultraviolet light towards the interior side 13 of the grating 10. In the grating 10, the ultraviolet light is passed on all the way to the exterior side 15 of the grating 10 through the transparent portions 16 of the elements 11 of the grating 10. In this way, anti-biofouling of the entire grating 10 is realized, so that the capability of the opening 31 in which the grating 10 is present to allow water to enter and/or to exit the sea chest 34 is preserved. Examples of the way in which the ultraviolet light may travel through an element 11 at a position where the element 11 comprises a combination of a transparent portion 16 and a non-transparent portion 17 are shown in FIG. 4, the rays being depicted like arrows. Especially, in FIG. 4, a cross-sectional view of the element 11 is shown, so that it may be clear that some of the light follows such a path that the non-transparent portion 17 is not encountered, and that some of the light does encounter the non-transparent portion 17, but may reach the exterior side 15 of the grating 10 anyway on the basis of reflection on the non-transparent portion 17 and further travel through the transparent portion 16.

Figure 5:
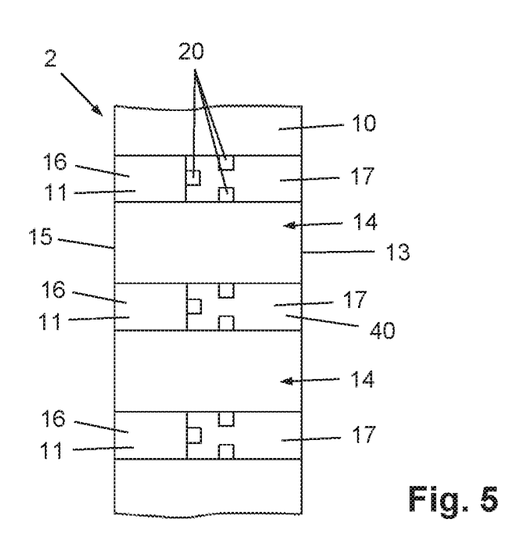
FIG. 5 relates to an assembly of a grating and at least one anti-biofouling source according to a second embodiment of the invention in which a plurality of anti-biofouling sources are integrated in the grating, wherein the figure diagrammatically shows a side view of a portion of the assembly.

Like the assembly 1 according to the first embodiment of the invention, the assembly 2 according to the second embodiment of the invention comprises a grating 10 and at least one anti-biofouling source 20. A difference between the two embodiments resides in the fact that in the second embodiment, the at least one anti-biofouling source 20 is integrated in the grating 10. The second embodiment may still comprise one or more anti-biofouling sources 20 arranged outside of the grating 10, but it is preferred for all anti-biofouling sources 20 of the assembly 2 to be integrated in the grating 10 in order to dispense with a need for measures aimed at realizing a stable positioning of the anti-biofouling sources 20 inside the sea chest 34. Also, the anti-biofouling sources 20 are very well protected against possible damage in the case of the integrated arrangement of the anti-biofouling sources 20 in the grating 10.

FIG. 5 illustrates how the integrated arrangement of the anti-biofouling sources 20 in the grating 10 may be realized. In the shown example, the elements 11 of the grating 10 comprise transparent portions 16 and non-transparent portions 17, wherein the non-transparent portions 17 are positioned at the interior side 13 of the grating 10, and the transparent portions 16 are positioned at the exterior side 15 of the grating 10. Each of the non-transparent portions 17 is provided with a number of recesses for accommodating anti-biofouling sources 20. The number of recesses and the associated number of anti-biofouling sources 20 per non-transparent portion 17 can be chosen freely within the framework of the invention. Also, it is not essential that every non-transparent portion 17 is equipped with at least one anti-biofouling source 20, although this is preferred for obtaining optimal anti-biofouling results at a minimum of power consumption. The anti-biofouling sources 20 may be provided in the form of LEDs for emitting ultraviolet light. It is practical for each of the elements 11 of the grating 10 to be provided with arrays of LEDs, extending in the longitudinal direction of the elements 11. In the shown example, complete coverage of the grating 10 for anti-biofouling purposes is obtained by having LEDs in the sides of the non-transparent portions 17 of the elements 11 facing each other and the side of the non-transparent portions 17 facing the transparent portions 16. As is the case with the grating 10 of the assembly 1 according to the first embodiment of the invention, the grating 10 of the assembly 2 according to the second embodiment of the invention can be sufficiently strong due to the presence of the non-transparent portions 17 of the elements 11 thereof, constituting a carrier frame 40, and can also be effective in staying clean under the influence of the ultraviolet light, the anti-biofouling sources 20 being distributed over the carrier frame 40.

In a practical embodiment, the grating 10 of the assembly 1, 2 according to the invention may comprise a metal carrier frame 40 with silicones or Teflon. Possibly also sandwiches of silicon and quartz could be applied in a way as known per se from the field of safety windows.

The invention is applicable to a ship as described in the foregoing, or to any other type of vessel, i.e. watercraft.

It will be clear to a person skilled in the art that the scope of the invention is not limited to the examples discussed in the foregoing, but that several amendments and modifications thereof are possible without deviating from the scope of the invention as defined in the attached claims. It is intended that the invention be construed as including all such amendments and modifications insofar they come within the scope of the claims or the equivalents thereof. While the invention has been illustrated and described in detail in the figures and the description, such illustration and description are to be considered illustrative or exemplary only, and not restrictive. The invention is not limited to the disclosed embodiments. The drawings are schematic, wherein details that are not required for understanding the invention may have been omitted, and not necessarily to scale.

Variations to the disclosed embodiments can be understood and effected by a person skilled in the art in practicing the claimed invention, from a study of the figures, the description and the attached claims. In the claims, the word "comprising" does not exclude other steps or elements, and the indefinite article "a" or "an" does not exclude a plurality. Any reference signs in the claims should not be construed as limiting the scope of the invention. The phrase "a plurality of" as used in this text should be understood such as to mean "at least two".

Elements and aspects discussed for or in relation with a particular embodiment may be suitably combined with elements and aspects of other embodiments, unless explicitly stated otherwise. Thus, the mere fact that certain measures are recited in mutually different dependent claims does not indicate that a combination of these measures cannot be used to advantage.

The term "substantially" as used in this text will be understood by a person skilled in the art as being applicable to situations in which a certain effect is intended which can be fully realized in theory but which involves practical margins for its factual implementation. Examples of such an effect include a parallel arrangement of objects and a perpendicular arrangement of objects. Where applicable, the term "substantially" may be understood such as to be an adjective which is indicative of a percentage of 90% or higher, such as 95% or higher, especially 99% or higher, even more especially 99.5% or higher, including 100%.

The term "comprise" as used in this text will be understood by a person skilled in the art as covering the term "consist of". Hence, the term "comprise" may in respect of an embodiment mean "consist of", but may in another embodiment mean "contain/include at least the defined species and optionally one or more other species".

In view of the fact that biofouling does not only occur at sea, but also in rivers, lakes, basins and the like, the measures according to the invention are generally applicable in a context in which an opening for allowing water to pass therethrough is present. Examples of such a context include the context of marine objects such as oilrigs, or other types of buildings and constructions in or next to the ocean/sea, and the context of water cooling systems of power plants. In fact, the measures of the invention can be put to practice in every situation in which a grating is present and in which the grating is exposed to water during at least a part of its lifetime, such that the grating may suffer from biofouling as a consequence thereof.

Summarizing, a vessel has a compartment 34 for containing water, which compartment 34 is delimited by a portion of the vessel's hull 30 and an interior wall arrangement 33 of the vessel connecting to the hull 30, and which compartment 34 has at least one opening 31 in a wall 30 thereof for allowing water to pass therethrough. The compartment 34 comprises an assembly 1, 2 of a grating 10 and at least one anti-biofouling source 20, the grating 10 being positioned in the opening 31 for blocking items from passing through the opening 31 along with the water, and comprising a number of elements 11 and spaces 14 between the elements 11, and the anti-biofouling source 20 being configured to emit ultraviolet light during operation thereof for realizing anti-biofouling of at least a portion of the grating 10. At least one of the elements 11 of the grating 10 is at least partially transparent to the ultraviolet light, enabling a design of the assembly 1, 2 in which anti-biofouling of the entire grating 10 may be guaranteed, even in case the at least one anti-biofouling source 20 is positioned at only one side 13 of the grating 10 and/or inside the grating 10.

The invention claimed is:

1. An object comprising:
   at least one opening, wherein the opening is arranged to allow a fluid to to pass therethrough; and
   an assembly, the assembly comprising a grating and at least one anti-biofouling source,
   wherein the grating is positioned in the opening, wherein the grating comprises a number of elements and spaces between the elements, wherein the anti biofouling source is configured to emit ultraviolet light during operation such that is realizes anti-biofouling of at least a portion of the grating, wherein at least one of the elements of the grating is at least partially transparent to the ultraviolet light.

2. The object of claim 1, wherein the object a building in proximity to large body of water.

3. The object of claim 1, wherein the object is a vessel having a compartment, wherein the compartment is delimited by a portion of the vessel and an interior wall arrangement of the vessel connecting to the portion of the vessel, wherein the compartment comprises the at least one opening.

4. The object according to claim 1, wherein at least one anti-biofouling source of the assembly is integrated in the grating.

5. The object according to claim 1, wherein the assembly comprises a plurality of anti-biofouling sources which are integrated in the grating.

6. The object according to claim 3, wherein at least one anti-biofouling source of the assembly is positioned inside the compartment.

7. The object according to claim 6, wherein the at least one anti-biofouling source which is positioned inside the compartment is associated with the wall of the compartment.

8. The object according to claim 1, wherein the grating comprises a carrier frame, wherein at least two portions of the grating are transparent to the ultraviolet light, wherein the at least two portions transparent are distributed over the carrier frame.

9. The object according to claim 8, wherein at least one anti-biofouling source of the assembly is integrated in the carrier frame.

10. The object according to claim 8, wherein the assembly comprises a plurality of anti-biofouling sources, wherein the plurality of anti-biofouling sources are integrated in the carrier frame.

11. The object according to claim 8, wherein the carrier frame of the grating is not transparent to the ultraviolet light.

12. The object according to claim 8, wherein the carrier frame of the grating is made of metal.

13. The object of claim 1, wherein the object is a water cooling system of a power plant.

* * * * *